(12) United States Patent
Khoo (10) Patent No.: US 8,070,779 B2
(45) Date of Patent: Dec. 6, 2011

(54) PERCUTANEOUS INTERSPINOUS PROCESS DEVICE AND METHOD

(75) Inventor: Larry Khoo, Studio City, CA (US)

(73) Assignee: K2M, Inc., Leesburg, VA (US)

( * ) Notice: Subject to any disclaimer, the term of this patent is extended or adjusted under 35 U.S.C. 154(b) by 385 days.

(21) Appl. No.: 12/132,951

(22) Filed: Jun. 4, 2008

(65) Prior Publication Data

US 2008/0300686 A1    Dec. 4, 2008

Related U.S. Application Data

(60) Provisional application No. 60/933,028, filed on Jun. 4, 2007.

(51) Int. Cl.
*A61B 17/70* (2006.01)
(52) U.S. Cl. .......... 606/249; 606/248; 606/246
(58) Field of Classification Search .......... 623/17.11, 623/17.16; 606/246–279
See application file for complete search history.

(56) References Cited

U.S. PATENT DOCUMENTS

| | | | |
|---|---|---|---|
| 5,496,318 A | 3/1996 | Howland et al. | |
| 5,609,634 A | 3/1997 | Voydeville | |
| 5,645,599 A | 7/1997 | Samani | |
| 6,364,883 B1 | 4/2002 | Santilli | |
| 6,451,020 B1 * | 9/2002 | Zucherman et al. | 606/249 |
| 6,582,433 B2 | 6/2003 | Yun | |
| 6,626,944 B1 | 9/2003 | Taylor | |
| 6,695,842 B2 | 2/2004 | Zucherman et al. | |
| 6,733,534 B2 | 5/2004 | Sherman | |
| 6,902,566 B2 | 6/2005 | Zucherman et al. | |
| 6,946,000 B2 | 9/2005 | Senegas et al. | |
| 6,974,478 B2 | 12/2005 | Reiley et al. | |
| 7,087,055 B2 | 8/2006 | Lim et al. | |
| 7,087,083 B2 | 8/2006 | Pasquet et al. | |
| 7,163,558 B2 | 1/2007 | Senegas et al. | |
| 7,238,204 B2 | 7/2007 | Le Couedic et al. | |
| 2001/0012938 A1 | 8/2001 | Zucherman et al. | |
| 2002/0026197 A1* | 2/2002 | Foley et al. | 606/105 |
| 2002/0029039 A1 | 3/2002 | Zucherman et al. | |
| 2002/0099377 A1 | 7/2002 | Zucherman et al. | |
| 2002/0116000 A1 | 8/2002 | Zucherman et al. | |
| 2002/0143331 A1 | 10/2002 | Zucherman et al. | |
| 2002/0147449 A1 | 10/2002 | Yun | |
| 2003/0032959 A1 | 2/2003 | Yeh | |
| 2003/0040746 A1 | 2/2003 | Mitchell et al. | |
| 2003/0040799 A1* | 2/2003 | Boyd et al. | 623/17.11 |
| 2003/0060886 A1* | 3/2003 | Van Hoeck et al. | 623/17.11 |
| 2003/0065330 A1 | 4/2003 | Zucherman et al. | |
| 2003/0187435 A1 | 10/2003 | Liu | |
| 2003/0216736 A1 | 11/2003 | Robinson et al. | |

(Continued)

*Primary Examiner* — Todd Manahan
*Assistant Examiner* — Nicholas Plionis
(74) *Attorney, Agent, or Firm* — Carter, DeLuca, Farrell & Schmidt, LLP (57) ABSTRACT

A percutaneous interspinous process device for treating spinal conditions includes a first section, a second section, and a locking mechanism. The first section defines a first lateral surface, a first medial surface and a first lumen extending from the first lateral surface to the first medial surface. The second section defines a second lateral surface, a second medial surface and a second lumen extending from the second lateral surface. The locking mechanism includes an elongate member protruding from the first medial surface of the first section and a medial recess defined in the second medial surface of the second section. The medial recess is configured for securely receiving at least a portion of the elongate member. The elongate member is configured to define a space between adjacent spinous processes and maintain a predetermined distance between adjacent spinous processes.

26 Claims, 9 Drawing Sheets

U.S. PATENT DOCUMENTS

| | | |
|---|---|---|
| 2003/0225416 A1 | 12/2003 | Bonvallet et al. |
| 2004/0097931 A1 | 5/2004 | Mitchell |
| 2004/0106927 A1 | 6/2004 | Ruffner et al. |
| 2005/0075634 A1 | 4/2005 | Zucherman et al. |
| 2005/0165398 A1 | 7/2005 | Reiley |
| 2005/0203512 A1 | 9/2005 | Hawkins et al. |
| 2005/0209603 A1 | 9/2005 | Zucherman et al. |
| 2005/0245929 A1 | 11/2005 | Winslow et al. |
| 2005/0245937 A1 | 11/2005 | Winslow et al. |
| 2005/0261768 A1 | 11/2005 | Trieu |
| 2005/0288672 A1 | 12/2005 | Ferree |
| 2006/0036240 A1 | 2/2006 | Colleran et al. |
| 2006/0036246 A1 | 2/2006 | Carl et al. |
| 2006/0036258 A1 * | 2/2006 | Zucherman et al. ............ 606/90 |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0089718 A1 | 4/2006 | Zucherman et al. |
| 2006/0106381 A1 | 5/2006 | Ferree et al. |
| 2006/0136060 A1 | 6/2006 | Taylor |
| 2006/0142759 A1 | 6/2006 | Arnin et al. |
| 2006/0235386 A1 | 10/2006 | Anderson |
| 2006/0235387 A1 | 10/2006 | Peterman |
| 2006/0235532 A1 | 10/2006 | Meunier et al. |
| 2006/0241757 A1 | 10/2006 | Anderson |
| 2006/0247623 A1 | 11/2006 | Anderson et al. |
| 2006/0247634 A1 | 11/2006 | Warner et al. |
| 2006/0247640 A1 * | 11/2006 | Blackwell et al. ............... 606/71 |
| 2006/0259037 A1 | 11/2006 | Hartmann et al. |
| 2006/0259142 A1 | 11/2006 | Dooris et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271194 A1 | 11/2006 | Zucherman et al. |
| 2006/0282079 A1 | 12/2006 | Labrom et al. |
| 2006/0293662 A1 | 12/2006 | Boyer et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0055246 A1 | 3/2007 | Zucherman et al. |
| 2007/0055373 A1 | 3/2007 | Hudgins et al. |
| 2007/0073292 A1 | 3/2007 | Kohm et al. |
| 2007/0073405 A1 | 3/2007 | Verhulst et al. |
| 2007/0083200 A1 | 4/2007 | Gittings et al. |
| 2007/0088358 A1 | 4/2007 | Yuan et al. |
| 2007/0093823 A1 | 4/2007 | Booth et al. |
| 2007/0093825 A1 | 4/2007 | Ferree et al. |
| 2007/0093830 A1 | 4/2007 | Zucherman et al. |
| 2007/0118120 A1 | 5/2007 | Stevenson et al. |
| 2007/0123861 A1 | 5/2007 | Dewey et al. |
| 2007/0149972 A1 | 6/2007 | Nakajima et al. |
| 2007/0161991 A1 | 7/2007 | Altarac et al. |
| 2007/0161992 A1 | 7/2007 | Kwak et al. |
| 2007/0161993 A1 | 7/2007 | Lowery et al. |
| 2007/0162000 A1 | 7/2007 | Perkins |
| 2007/0167945 A1 | 7/2007 | Lange et al. |
| 2007/0168035 A1 | 7/2007 | Koske |
| 2007/0168039 A1 | 7/2007 | Trieu |
| 2007/0173818 A1 | 7/2007 | Hestad et al. |
| 2007/0173821 A1 | 7/2007 | Trieu |
| 2007/0173823 A1 | 7/2007 | Dewey et al. |
| 2007/0173832 A1 | 7/2007 | Tebbe et al. |
| 2007/0179500 A1 | 8/2007 | Chin et al. |
| 2007/0185490 A1 | 8/2007 | Implicito |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0191959 A1 | 8/2007 | Hartmann et al. |
| 2007/0203495 A1 | 8/2007 | Zucherman et al. |
| 2007/0213739 A1 | 9/2007 | Michelson et al. |

\* cited by examiner

PERCUTANEOUS INTERSPINOUS PROCESS DEVICE AND METHOD

CROSS-REFERENCE TO RELATED APPLICATION

This application claims priority to, and the benefit of, U.S. Provisional Patent application 60/933,028, filed on Jun. 4, 2007 the entire contents of which are incorporated herein by reference.

BACKGROUND

1. Technical Field

The present disclosure relates generally to devices and methods for treating spinal conditions, and more particularly, for treating spinal compression with percutaneous spinal devices implanted between adjacent spinous processes.

2. Background of the Related Art

A significant number of people suffer from a condition known as spinal stenosis. Spinal stenosis is a progressive narrowing of the spinal canal that causes compression of the spinal cord. Each vertebra in the spinal column has an opening that extends through it. These openings are aligned vertically to form the spinal canal. The spinal cord runs through the spinal canal. As the spinal canal narrows due to spinal stenosis, the spinal cord and the nerve roots extending therefrom are compressed. The compression of the spinal cord, the spinal nerve roots, or both, generally results in pain, weakness, numbness, burning sensations, tingling, and, in particularly severe cases, may cause loss of bladder or bowel function, or paralysis. The legs, calves, and buttocks are most commonly affected by spinal stenosis; however, the shoulders and arms may also be affected if the stenosis is in the cervical spine.

Mild cases of spinal stenosis may be treated with rest or restricted activity, non-steroidal anti-inflammatory drugs (e.g., aspirin), corticosteroid injections (epidural steroids), physical therapy, or any combination thereof. A patient suffering from spinal stenosis may find temporary comfort or relieve from the pain by bending forward, sitting, or lying down. These actions may ephemerally increase the vertebral space and thus relieve nerve compression. Given that spinal stenosis is generally a progressive disease, the source of pressure may have to be surgically corrected (e.g. decompressive laminectomy) as the disease worsens. A surgical intervention may remove bone and other tissue that has been impinged or compressed the spinal canal. Two adjacent vertebrae may also be fused during the surgical procedure to prevent instability, improper alignment, or slippage. Surgical decompression may relieve pressure on the spinal cord or spinal nerve roots by widening the spinal canal and creating more space.

Minimally-invasive surgical procedures and devices have been developed over the years to treat spinal stenosis and other spinal conditions. Although scientists and engineers have made significant advances, improvements are still possible.

SUMMARY

A percutaneous interspinous process device for treating spinal conditions includes a first section defining a first lateral surface, a first medial surface and a first lumen extending from the first lateral surface to the first medial surface. The first medial surface has a plurality of first teeth adapted for engaging tissue. The percutaneous interspinous process device further includes a second section defining a second lateral surface, a second medial surface and a second lumen extending from the second lateral surface. The second medial surface includes a plurality of second teeth adapted for engaging tissue. In addition, the percutaneous interspinous process device has a locking mechanism configured to maintain a relative position between first and second sections.

The percutaneous interspinous process device described above may be included into a surgical kit with a sizing instrument configured for determining the appropriate size of the percutaneous interspinous process device. In use, the sizing instrument measures a space between adjacent spinous processes so that the appropriate implant with the correctly dimensioned first and second sections, and specifically the central longitudinal section, can be selected.

The present disclosure further relates to a method for implanting a spinal implant between adjacent spinous processes. This method includes the steps of providing a spinal implant having first and second sections configured to connect with each other, distracting adjacent spinous processes, thereby increasing a distance between adjacent spinous processes, inserting the first section of the spinal implant from a first lateral position and into a space between adjacent spinous processes, inserting the second section of the spinal implant from a second lateral position and into the space between adjacent spinous processes, and connecting first and second sections of the spinal implant. Preferably, the first and second sections of the implant are introduced percutaneously from opposite lateral aspects of the patient's spine, and joined together once positioned between the spinous processes. This approach has the advantage of leaving the posterior interspinous ligaments intact.

BRIEF DESCRIPTION OF THE FIGURES

Embodiments of the presently disclosed percutaneous interspinous process device are described herein with reference to the accompanying drawings, wherein.

DETAILED DESCRIPTION OF THE EMBODIMENTS

Embodiments of the presently disclosed percutaneous interspinous process device will now be described in detail with reference to the drawings, wherein like reference numerals identify similar or identical elements. In the drawings and in the description that follows, the term "proximal" will refer to the end of a surgical instrument or device that is closest to the operator, while the term "distal" will refer to the end of the instrument or device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

Figure 1:
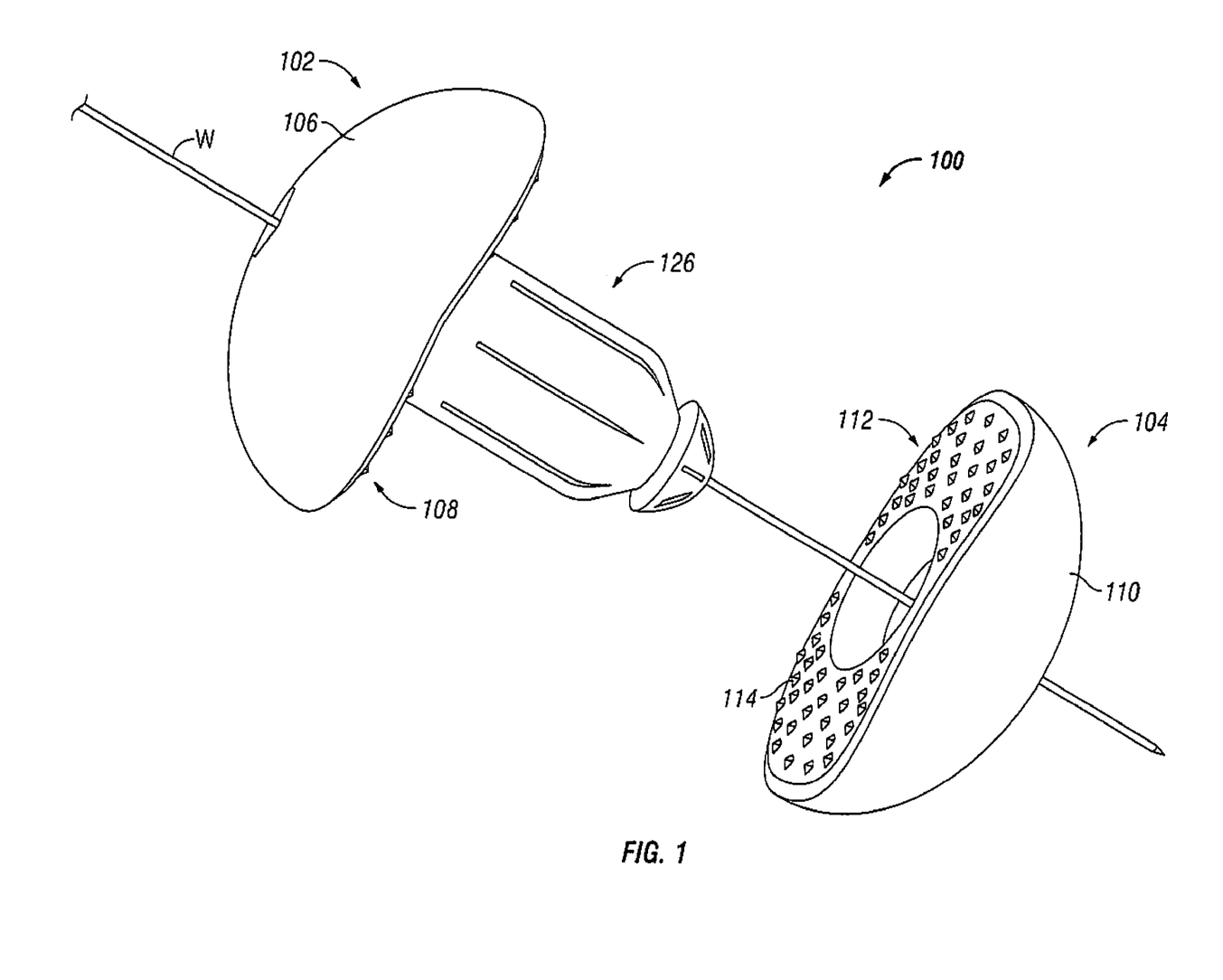
FIG. 1 is a perspective view of a percutaneous interspinous process device according to an embodiment of the present disclosure.

With reference to FIG. 1, a percutaneous interspinous process device or spinal implant is generally designated as 100. Physicians may use spinal implant 100 during minimally invasive surgical procedures to relieve pressure from the spinal cord, the spinal nerve roots, or both, by increasing the size of the opening through which the affected nerve exits. Surgeons may particularly employ spinal implant 100 to treat spinal stenosis. As discussed above, spinal stenosis is a degenerative disease, wherein the spinal canal narrows and causes compression of the spinal cord, the spinal nerve roots, or both. To surgically relieve pressure from the spinal cord or the spinal nerve roots, the surgeon places spinal implant 100 between adjacent spinal processes 'P' (see FIG. 7) to increase the size of the opening through which the nerve exits, thereby relieving pressure on the nerve which in turn should relieve the pain experienced by the patient during normal activities.

Spinal implant 100 may be made of any other suitable biocompatible material having the desired properties (stiffness, rigidity, flexibility, radiolucence, etc.). More specifically, implant 100 may be made of any suitable plastic (nylon, polyethylene, polyurethane, polyetheretherketone (PEEK), etc.), metal (titanium, titanium ally, stainless steel, nickel titanium, cobalt chrome, etc.) ceramic, composite or combinations thereof. Spinal implant 100 includes a first section 102 and a second section 104 configured to connect with each other. First section 102 has a lateral surface 106 and medial surface 108. Each of the first and second sections 102, 104 may be made of radiopaque or radiolucent materials. In use, lateral surface 106 faces laterally away from a patient's center, and medial surface 108 faces the spinal process 'P' and second section 104. Similarly, second section 104 contains a lateral surface 110 that faces away from the patient's center and a medial surface 112 that faces the spinal process 'P' and first section 102 during use.

Figure 3:
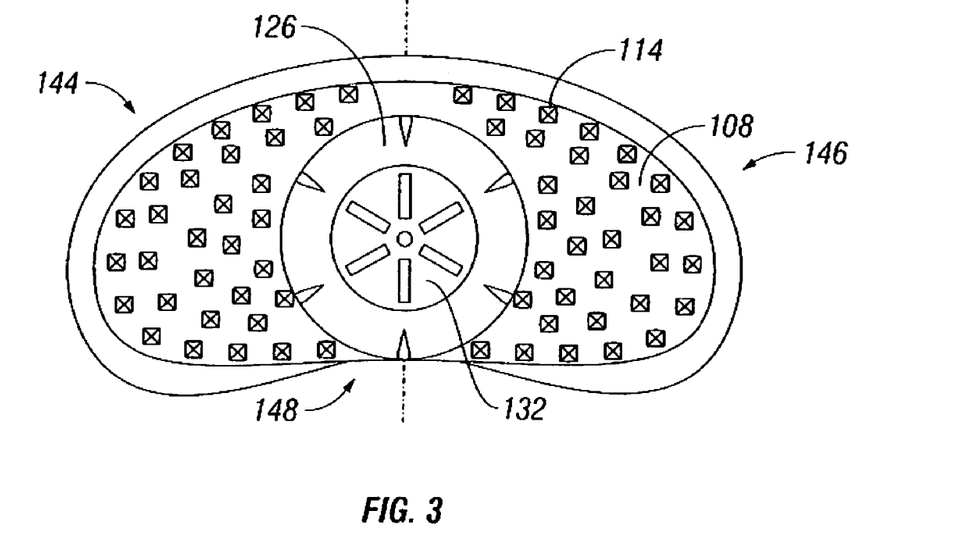
FIG. 3 is a medial end view of a first section of the percutaneous interspinous process device of FIG. 1.
Figure 4:
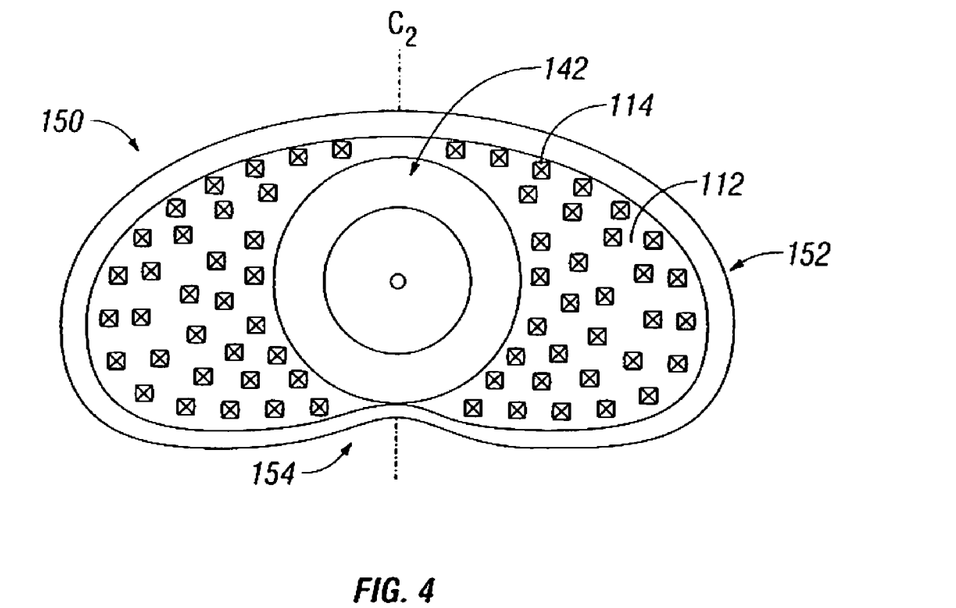
FIG. 4 is a medial end view of a second section of the percutaneous interspinous process device of FIG. 1.

Each of the medial surfaces 108, 112 includes a plurality of teeth 114 protruding therefrom, as seen in FIGS. 3 and 4. Teeth 114 are configured to engage tissue and facilitate attachment of spinal implant 100 to the spinal processes 'P'. After spinal implant 100 has been implanted in the patient's body, teeth 114 secure spinal implant 100 to spinal processes P and hinders movement of spinal implant 100 within the patient's body. Teeth 114 may have a pyramid shape or any other suitable shape. Instead of or in addition to teeth 114, the first and second sections 102, 104 may include any other suitable fixation structure such as parallel ridges, holes or cavities for bone ingrowth, or through hole for placing a screw into the bone.

Figure 2:
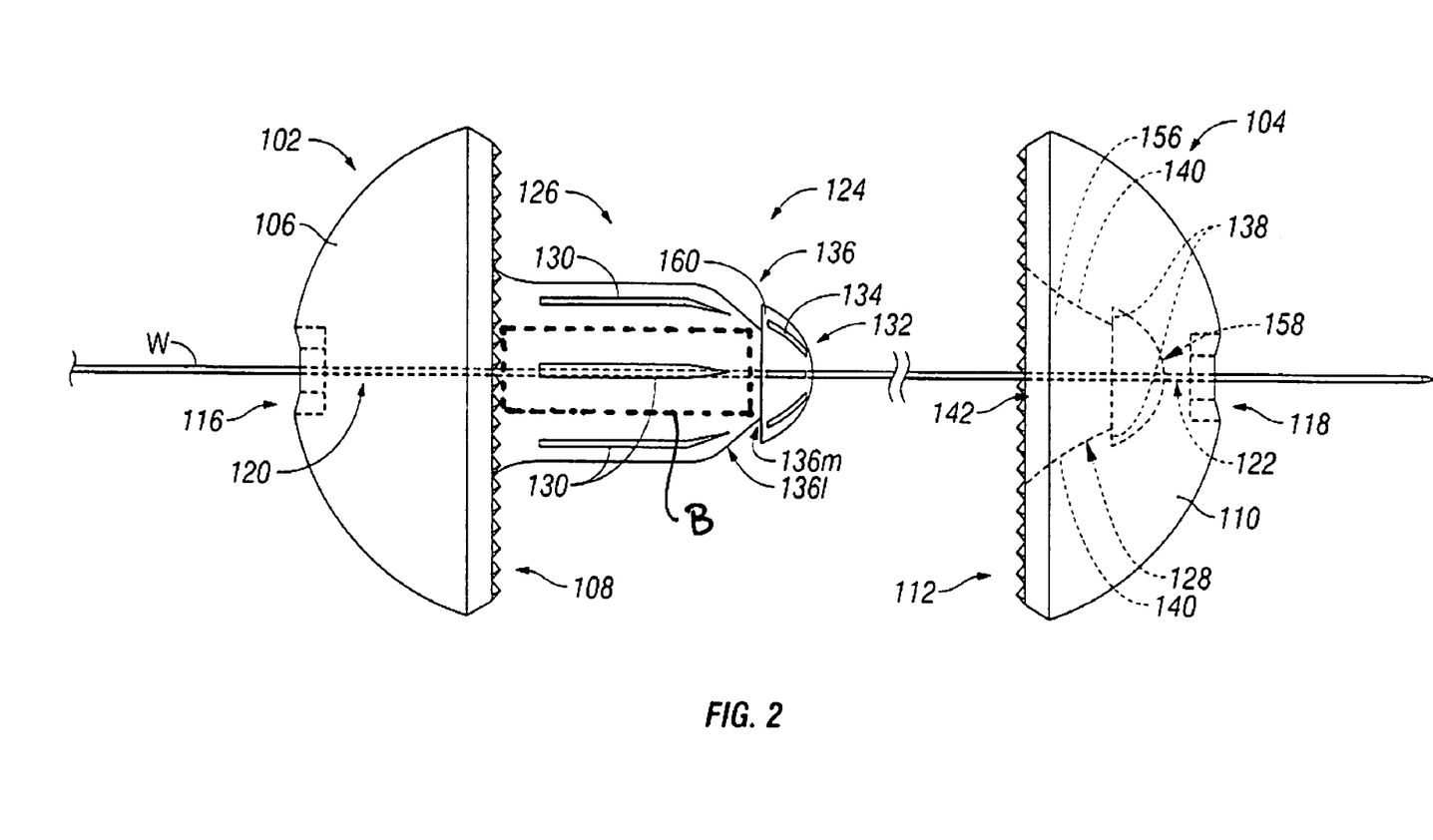
FIG. 2 is a side view of the percutaneous interspinous process device of FIG. 1.

With reference to FIG. 2, lateral surfaces 106, 110 of corresponding first and second sections 102, 104 may each have a convex shape. In one embodiment, the convex shape of lateral surfaces 106, 110 minimizes irritation of the soft tissue. Further, each lateral surface 106, 110 defines a recess 116, 118 adapted to receive an insertion instrument such as a conventional cup inserter (not shown). Recesses 116, 118 may have a hexagonal cross-section for facilitating reception of a hex-head of a screwdriver or any other suitable insertion instrument. In use, a physician places a portion of the insertion instrument in appropriate recess 116, 118 and then advances either first or second sections 102, 104 toward the spinal column of a patient.

First section 102 further defines lumen 120 extending therethrough and adapted to receive a guidewire 'W' such as a Kirschner wire ("K-wire"). Similarly, second section 104 defines a lumen 122 extending therethrough. Lumen 122 of second section 104 is also adapted to receive guidewire 'W' such as a K-wire. In use, lumens 120. 122 allow a surgeon to slide first and second sections 102, 104 of spinal implant 100 over guidewire 'W' to reach a predetermined surgical site. Usually, the physician inserts guidewire 'W' into the desired surgical site, and the physician then slides first and second sections 102, 104 of spinal implant 100 over guidewire 'W' toward each other to position spinal implant 100 in the desired location.

In addition to lumens 120, 122, spinal implant 100 includes a locking mechanism 124 for maintaining a relative distance between first and second sections 102, 104. In the depicted embodiment, locking mechanism 124 is a snap fit lock and includes an elongate member 126 protruding from medial surface 108 of first section 102 and an opening 142 defined in medial surface 112 of second section 104. Opening 142 leads to a recess 128 configured for securely receiving at least a portion of elongate member 126. Elongate member 126 includes slits 130 disposed around its periphery. Slits 130 permit elastic and radial expansion and compression of elongate member 126 when elongate member 126 is subjected to cyclical loads. Although the drawings show elongate member 126 with longitudinal slits 130, elongate member 126 may include spiral slits, radial slits, a combination of longitudinal and radial slits, or any combination thereof. While elongate member 126 radially expands or compresses, the cross-sectional area of elongate member 126 increases or decreases. When spinal implant 100 is implanted inside a patient's body, elongate member 126 distracts or maintains a predetermined distance between adjacent spinous processes, and slits 130 facilitate elastic distraction against the spinous processes to minimize the risk of bone fracture. Elongate member 126 may be hollow, thereby facilitating radial expansion and compression during use. In addition, elongate member 126 may be filled with a resilient material or may contain a compressible bladder 'B' (shown in phantom in FIG. 2) that defines the resistance of elongate member 126 to compression.

Elongate member 126 further contains a tapered portion 136 having medial and lateral ends 136*m*, 136*l*. The cross-sectional area of the tapered portion 136 decreases from lateral end 136*l* to medial 136*m*. Medial end 136*m* of tapered area 136 has a cross-sectional area that is smaller than the cross-sectional area of a barb or tapered tip 132 positioned at the medial end of elongate member 126. Barb 132 is configured for reception within recess 128 through opening 142 and defines a plurality of slits 134 around its periphery. Slits 134 allow radial compression and expansion of barb 132 during insertion through the space defined between adjacent spinous processes and into recess 128. Barb 132 may have a convex or dome shape, as shown in FIG. 2, or any other suitable shape or configuration.

As discussed above, recess 128 is adapted to receive at least barb 132 of elongate member 126. Recess 128 includes a frusto-conical region 156 for facilitating insertion of at least a portion of elongate member 126 and a dome-shaped region 158 for engaging barb 132. Dome-shaped region 158 defines abutting surfaces 138 adapted for supporting a flat lateral surface 160 of barb 132. Abutting surfaces 138 engage flat lateral surface 160, thereby securing barb 132 to second section 104 and maintaining a relative distance between first and sections 102, 104. Frusto-conical region 156 defines tapered surfaces 140 configured to facilitate insertion of at least a portion of elongate member 126 into recess 128 through opening 142.

Referring to FIGS. 3 and 4, medial surface 108 of first section 102 defines a central axis 'C1' passing along a central portion thereof and includes first and second wing 144, 146 extending outwardly relative to central axis 'C1'. Medial surface 108 further includes a concave portion 148 at a central portion thereof. In use, concave portion 148 faces in an anterior direction. When spinal implant 100 is attached to adjacent spinous processes of a patient, concave portion 148 and first and second wing 144, 146 substantially fit the curvature of the spinal lamina and inhibit rotation of spinal implant 100.

Like medial surface 108, medial surface 112 of second section 104 defines a central axis 'C2' passing along a central portion thereof and includes first and second wings 150, 152 extending outwardly relative to central axis 'C2'. Central axis 'C2' is substantially parallel to central axis 'C1'. Medial surface 112 also has a concave portion 154 adapted to fit anatomically the curvature of a spinal lamina. In use, concave portion 154 faces in an anterior direction. When spinal implant 100 is secured to adjacent spinous processes, concave portion 154 and first and second wings 144, 146 substantially fit the curvature of the spinal lamina and hinder rotation of spinal implant 100. Unlike medial surface 108, medial surface 112 defines an opening 142 dimensioned to receive elongate member 126, as discussed above. In the depicted embodiment, central axis 'C2' passes through the center of opening 142. Opening 142 may have a cross-sectional area large enough to receive elongate members 126 of different sizes. In one embodiment, opening 142 has a circular cross-sectional area with a 14 millimeter diameter. Those skilled in the art will recognize that opening 128 may have other shapes and sizes. In a similar vein, spinal implant 100 may come in a variety of sizes to adjust to different anatomies.

Figure 5:
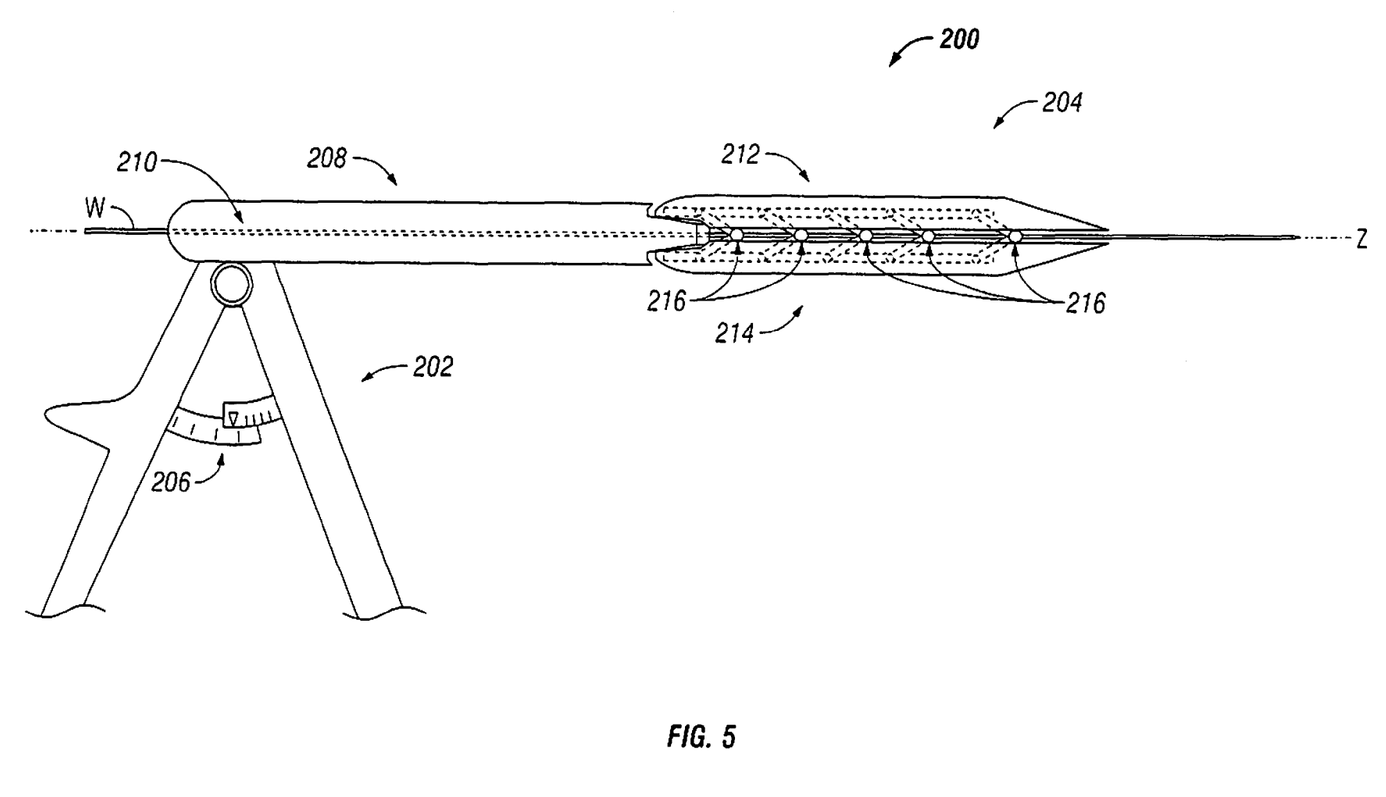
FIG. 5 is a side elevational view of an expandable interspinous sizing-distracting apparatus according to an embodiment of the present disclosure.

FIG. 5 illustrates a surgical instrument 200 capable of distracting adjacent spinous processes and sizing distance between those adjacent spinous processes. During operation, surgical instrument 200 distracts adjacent spinous processes and provides a means to determine the appropriate amount of distraction to be achieved between the spinous process and maintained by the implant 100. This measurement assists the surgeon in determining the appropriate spinal implant 100 to be used, and more specifically the diameter of the elongate portion 126 of implant 100 to be selected. The surgeon may place a trial implant between the distracted spinous processes to confirm the measurement before inserting the desired size spinal implant 100.

Surgical instrument 200 defines a longitudinal axis 'Z' along its length and includes a handle 202 that serves as an actuation mechanism for an end effector 204. Handle 202 may be a Kerrison type handle and includes a gauge 206 configured for measuring distances between adjacent spinous processes. Gauge 206 and handle 202 are both operatively associated with end effector 204. An elongate member 208 connects handle 202 to end effector 206. Moreover, elongate member 208 defines a lumen 210 extending therethrough and adapted to receive guidewire 'W'. End effector 204 consists of first and second jaws 212, 214 movable relative to each other while maintaining a substantially parallel arrangement. First and second jaws 212, 214 are configured to move simultaneously between a juxtaposed position (see FIG. 5) and a spaced apart position (see FIG. 6) with respect to each other upon actuation of handle 202. In operation, gauge 206 measures the distance between first and second jaws 212, 214. Together, first and second jaws 212, 214 define a tapered distal end. A plurality of hinges 216 pivotally couple first jaw 212 to second jaw 214.

Figure 6:
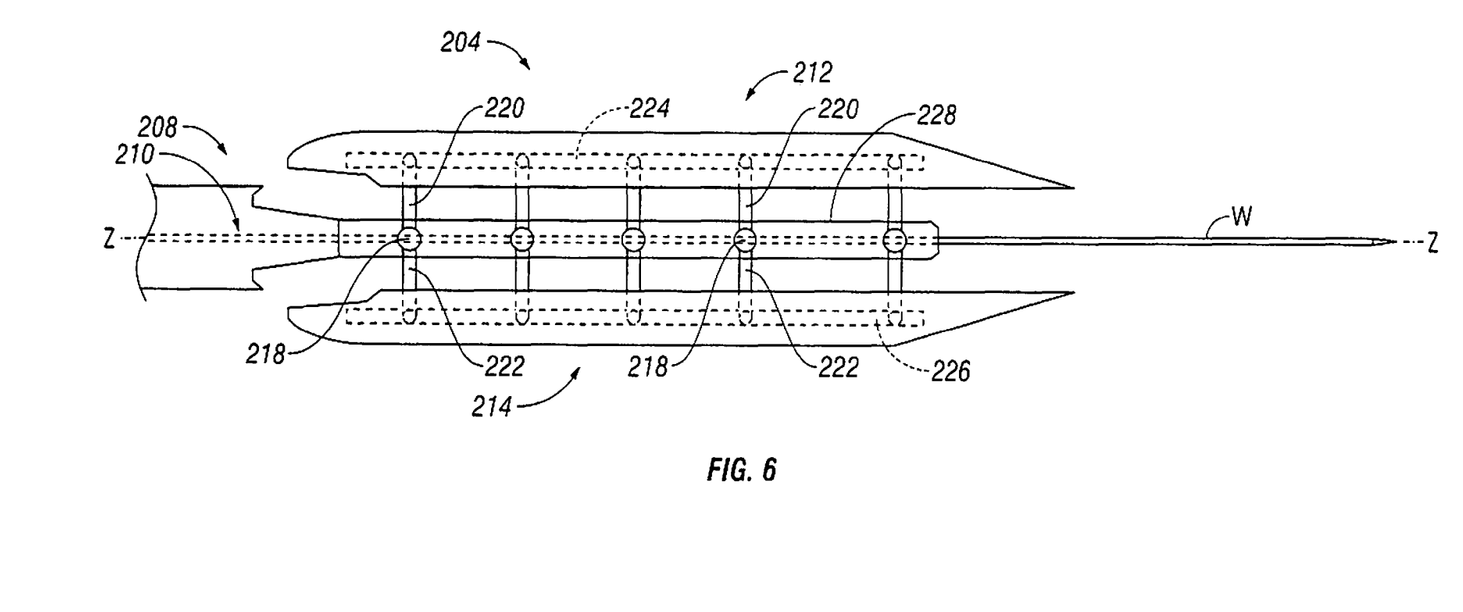
FIG. 6 is a side view of an end effector of the expandable interspinous sizing-distracting apparatus of FIG. 5, showing the end effector in an expanded position.

As best seen in FIG. 6, each hinge 216 has pivot pin 218 pivotally connecting first and second hinge leaves 220, 222 to a rod 228. Rod 228 defines a longitudinal passage for receiving guidewire 'W' and, during operation, moves longitudinally between a proximal position and a distal position in response to an actuation of handle 202. Each first hinge leaf 220 is connected to a first bar 224 fixed within first jaw 212. Similarly, each second hinge leaf 222 is coupled to a second bar 226 fixed within second jaw 214. First and second bars 224, 226 are both oriented substantially parallel to longitudinal axis 'Z'. When first and second jaws 212, 214 are juxtaposed with respect to each other, each of the first and second hinge leaves 220, 222 defines an oblique angle relative to longitudinal axis 'Z', as depicted in FIG. 5. Upon actuation of handle 202, rod 228 translates proximally and causes first hinge leaves 220 to pivot clockwise about corresponding pivot pins 218 and second hinge leaves 222 to pivot counterclockwise about corresponding pivot pins 218. While first hinge leaves 220 pivots clockwise and second hinge leaves 222 pivots counterclockwise, first and second jaws 212, 214 separate from each other. When first and second jaws 212, 214 are spaced apart from each other, first and second hinge leaves 220, 222 define a substantially perpendicular angle relative to longitudinal axis 'Z', as shown in FIG. 6.

Figure 7:
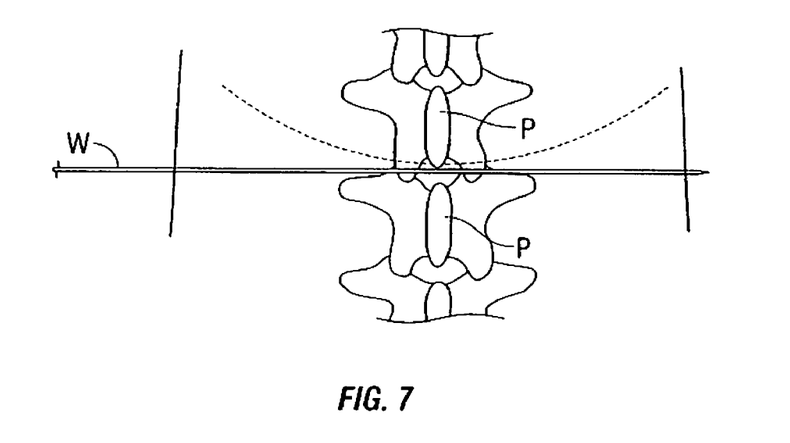
FIG. 7 is a posterior view depicting a step of a method for implanting the percutaneous interspinous process device of FIG. 1, showing a wire inserted percutaneously between adjacent spinous processes.

FIGS. 7-12 illustrate a method of implanting spinal implant 100 within a patient's body. In use, surgical instrument 200 assists in the insertion of spinal implant 100 into a space between adjacent spinal processes 'P'. Initially, the surgeon inserts guidewire 'W' percutaneously from a first lateral position until the guidewire 'W' passes through the space between adjacent spinous processes and reaches a second lateral position, as shown in FIG. 7. Optionally, the surgeon may alternatively employ a shielded guidewire and conduct an electromyogram ("EMG") through the shielded guidewire. In doing so, the surgeon tests the electrical activity of the spinal nerve roots and therefore assesses the physiologic properties of the spine nerve roots at rest and while contracting. Abnormal electrical activity in the spine nerve roots might indicate that a spine nerve root is irritated or pinched. After conducting the EMG, the physician may deem that the insertion of spinal implant 100 is appropriate.

Figure 8:
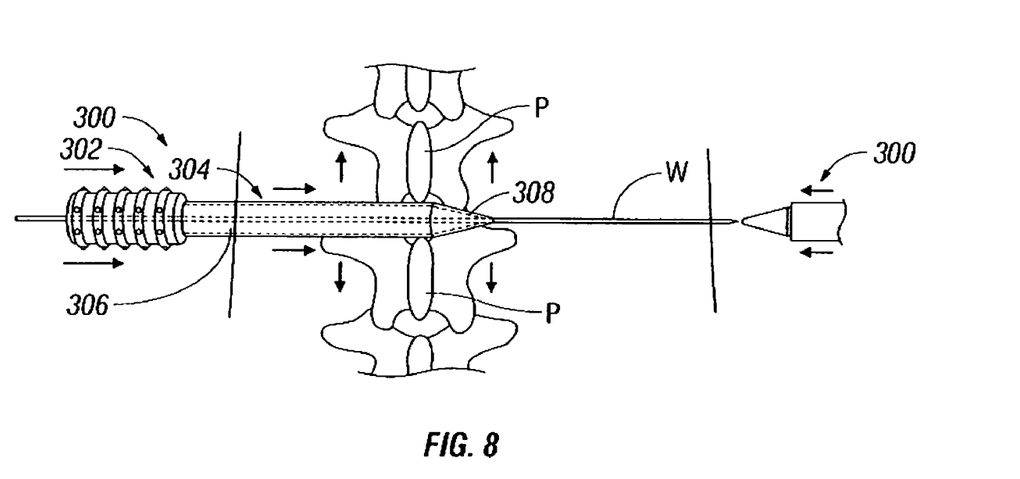
FIG. 8 is a posterior view illustrating a step of the method for implanting the percutaneous interspinous process device of FIG. 1, showing the insertion of a dilator over the wire.
Figure 9:
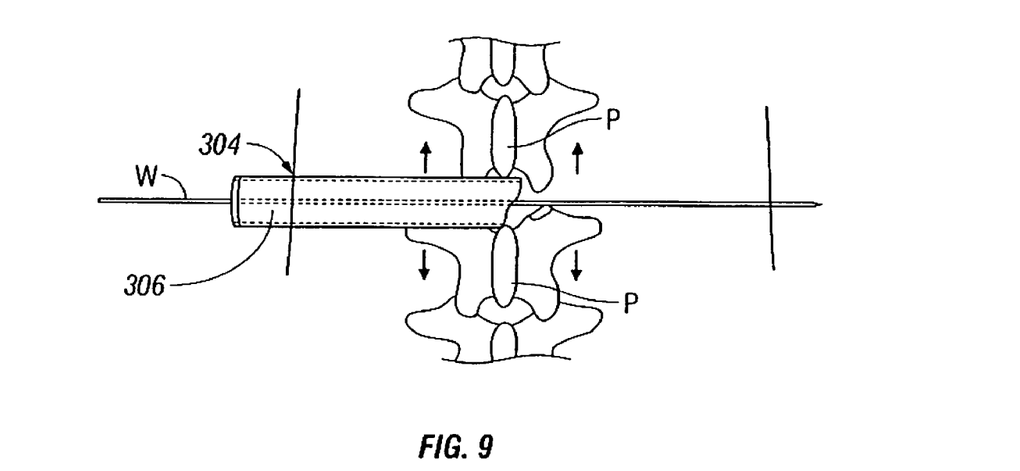
FIG. 9 is a posterior view illustrating a step of the method for implanting the percutaneous interspinous process device of FIG. 1, showing a sleeve of the dilator of FIG. 8 positioned over the wire.

Before inserting spinal implant 100 between adjacent spinous processes 'P', the surgeon may have to increase the distance between these two spinous processes 'P'. To this end, the surgeon inserts a dilator 300 over guidewire 'W' from the first and/or second lateral positions and toward the space between adjacent spinous processes 'P', as shown in FIG. 8. Dilator 300 includes first and second sleeves 302, 304 releasably connected to each other. First and second sleeves 302, 304 jointly define channel 306 extending therethrough. Channel 306 is adapted to receive at least a portion of surgical instrument 200. Second sleeve 304 contains a tapered distal tip 308 adapted for dilating tissue. During insertion of dilator 300, tapered distal tip 308 dilates the space between adjacent spinous processes 'P', as the surgeon moves dilator 300 from the first lateral position toward and into the space between adjacent spinous processes 'P.' The surgeon may also insert dilator 300 over guidewire 'W' horn the second lateral position and toward the space between adjacent spinous processes 'P'. Thereafter, the surgeon detaches first sleeve 302 from second sleeve 304 and leaves second sleeve 304 in place over the guidewire 'W', as illustrated in FIG. 9.

Figure 10:
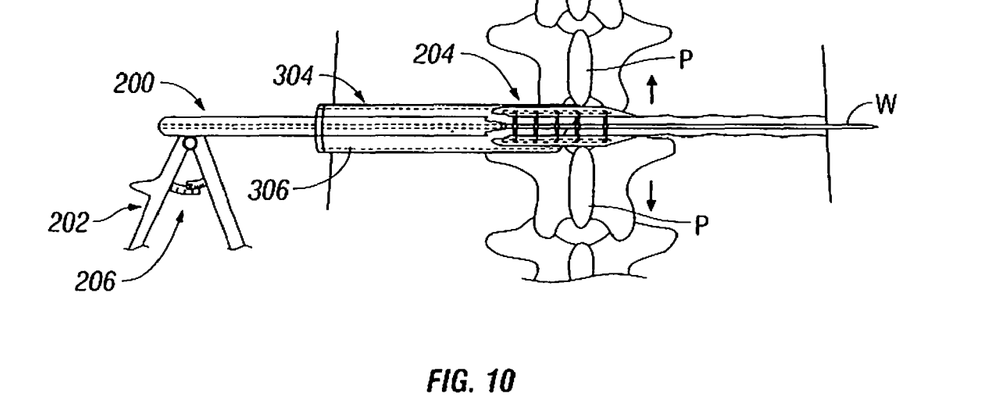
FIG. 10 is a posterior view illustrating a step of a method for implanting the percutaneous interspinous process device of FIG. 1, showing the distraction of adjacent spinous processes with the expandable interspinous sizing-distracting apparatus of FIG. 5.

Once the space between adjacent spinous processes 'P' has been dilated with dilator 300, the surgeon places at least a portion of surgical instrument 200 over guidewire 'W' and through channel 306 of second sleeve 304 until the at least tapered distal tip defined by first and second jaws 212, 214 is positioned between adjacent spinous processes 'P'. The physician then actuates handle 202 to move first and second jaws 212, 214 of end effector 204 from the juxtaposed position to the spaced apart position. The actuation of handle 202 increases the distance between first and second jaws 212, 214, thereby increasing the distance between adjacent spinous process 'P', as shown in FIG. 10. In addition, gauge 206 of surgical instrument 200 measures the distance between adjacent spinous process 'P'. After measuring the space between the distracted adjacent spinous processes 'P', the physician may insert a trial implant therebetween to confirm the measurement.

Figure 11:
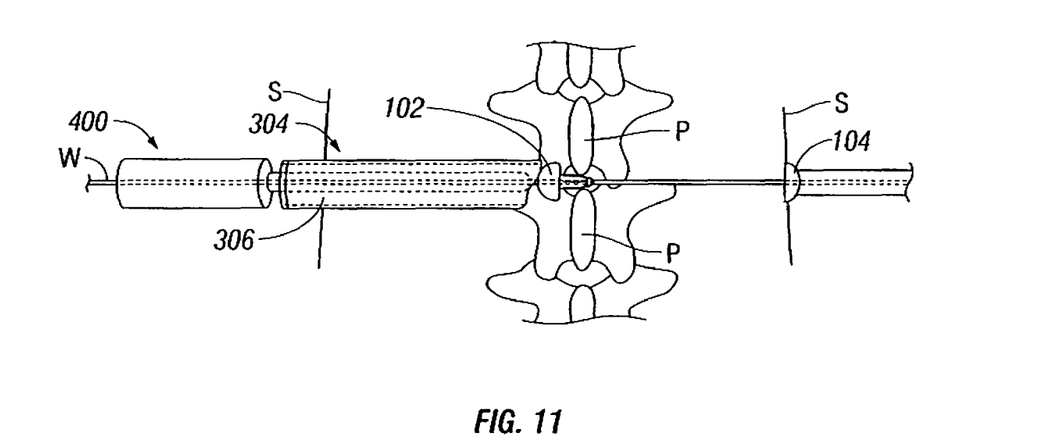
FIG. 11 is a posterior view illustrating a step of the method for implanting the percutaneous interspinous process device of FIG. 1, showing the percutaneous interspinous process device being implanted between adjacent spinous processes.
Figure 12:
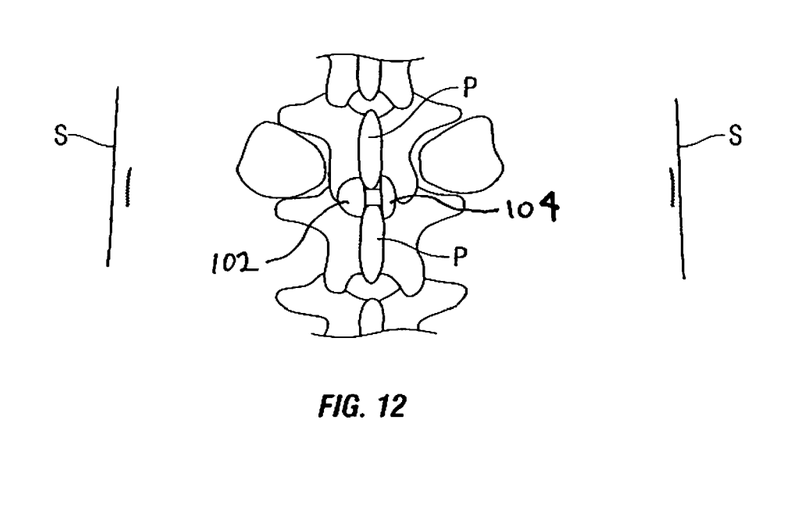
FIG. 12 is a posterior view illustrating a step of the method for implanting the percutaneous interspinous process device of FIG. 1, showing the percutaneous interspinous process implanted between adjacent spinous processes.

Following the measurement of the space between adjacent spinous processes 'P', the physician selects a spinal implant 100 suitable for the patient's anatomy and guides an insertion instrument 400, such as screwdriver or a cup inserter, over guidewire 'W' and through channel 306 of second sleeve 304 to advance first section 102 of spinal implant 100 toward the space between adjacent spinous processes 'P'. During this insertion process, at least a portion of elongate member 126 is specifically located between adjacent spinous processes 'P'. Barb 132 is not disposed between the adjacent spinous processes 'P'. Rather, barb 132 is positioned within dome-shaped region 158 of recess 128. This configuration avoids loading the barb 132 between the spinous processes. First section 102 is inserted from the first lateral position, and the second section 104 is inserted from the second lateral position, as seen in FIG. 11. The surgeon employs insertion instrument 400 to advance second section 104 of spinal implant 100 toward the adjacent spinal implant 100. The first and second sections 102, 104 are then connected and locked to each other to secure spinal implant 100 within the patient's body. After spinal implant 100 has been implanted, concave portions 148, 154 of first and second sections 102, 104 abut the opposed sides of spinal lamina. Subsequently, the surgeon removes guidewire 'W' from the patient's body and closes the incisions made on the skin 'S' during insertion, as shown in FIG. 12. Ideally, the posterior interspinous ligaments should be intact at the end of the above-described surgical procedure.

With reference to FIGS. 13-16, the surgeon may alternatively utilize a sizing-distracting instrument 500 for distracting adjacent spinal processes 'P' and/or sizing the space between adjacent spinal processes 'P'. Generally, instrument 500 includes a handle 502, an end effector 504, and an elongate portion 506 interconnecting handle 502 and end effector 504. Handle 502 includes a stationary handle member 508 and a movable handle member 510. A pivot pin 512, or any other suitable fastening member, pivotally connects movable handle 510 to stationary handle member 508. Movable handle 510 is operatively coupled to an actuation shaft 512. In one embodiment, a pin 514 operatively secures actuation shaft 512. During operation, a pivotal movement of movable handle member 510 toward stationary handle member 508 causes a distal translation of actuation shaft 512. Actuation shaft 512 extends from the handle 502 to end effector 504.

End effector 504, which is operatively connected to actuation shaft 512, includes first and second jaw members 516, 518 movable between spaced apart and approximated positions. A plurality of links 520 operatively couples first and second jaw members 516, 516 to a distal region 506d of elongate portion 506. Each link 520 has a proximal end 520p and a distal end 520d and defines a slot 522 disposed between proximal and distal ends 520p, 520d. The proximal ends 520p of each link 520 are pivotally connected to actuation shaft 512. On the other hand, at least one distal end 520d of links 520 is pivotally coupled to first jaw member 516, and at least one other distal end 520 of links 520 is pivotally attached to second jaw member 518. Pivot pins 524, or any other suitable fastening member, pivotally connect proximal ends 520p of links 520 to actuation shaft 512. Similarly, pivot pins 524 pivotally couple distal ends 520d of links 520 to first and second jaw members 516, 518.

A distal region 506d of elongate portion 506 is disposed between first and second jaw members 516, 518. Pins 526 operatively couple distal region 506d of elongate portion 506 to links 520. Each pin 526 is slidably positioned in slot 522 of each link 520. Moreover, each link 520 defines an oblique angle relative to actuation shaft 512.

Figures 13, 14:
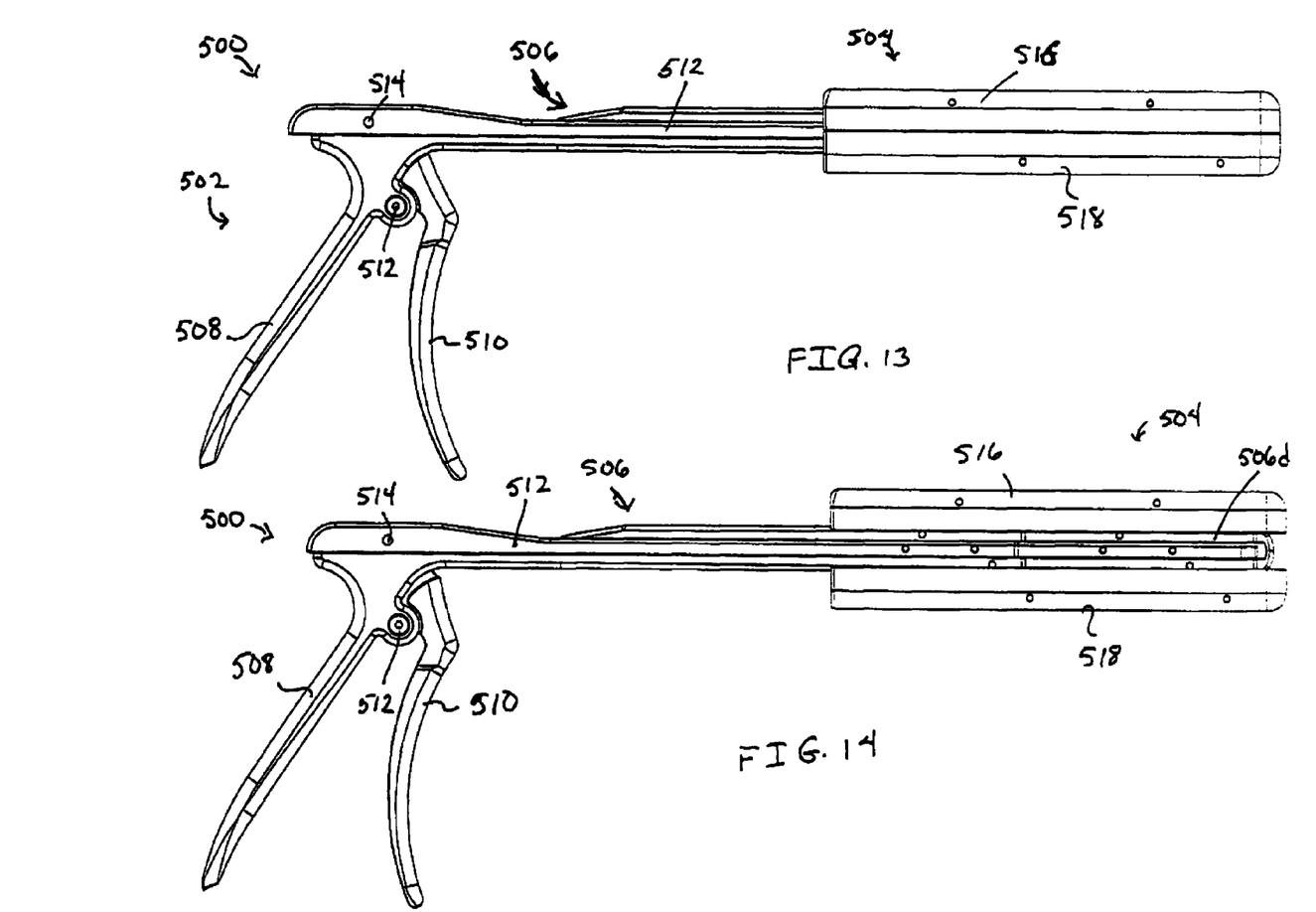
FIG. 13 is a side view of a sizing-distracting apparatus with the jaws in an approximated position.
FIG. 14 is a side view of the sizing-distracting apparatus with the jaws in the spaced apart position.
Figures 15, 16:
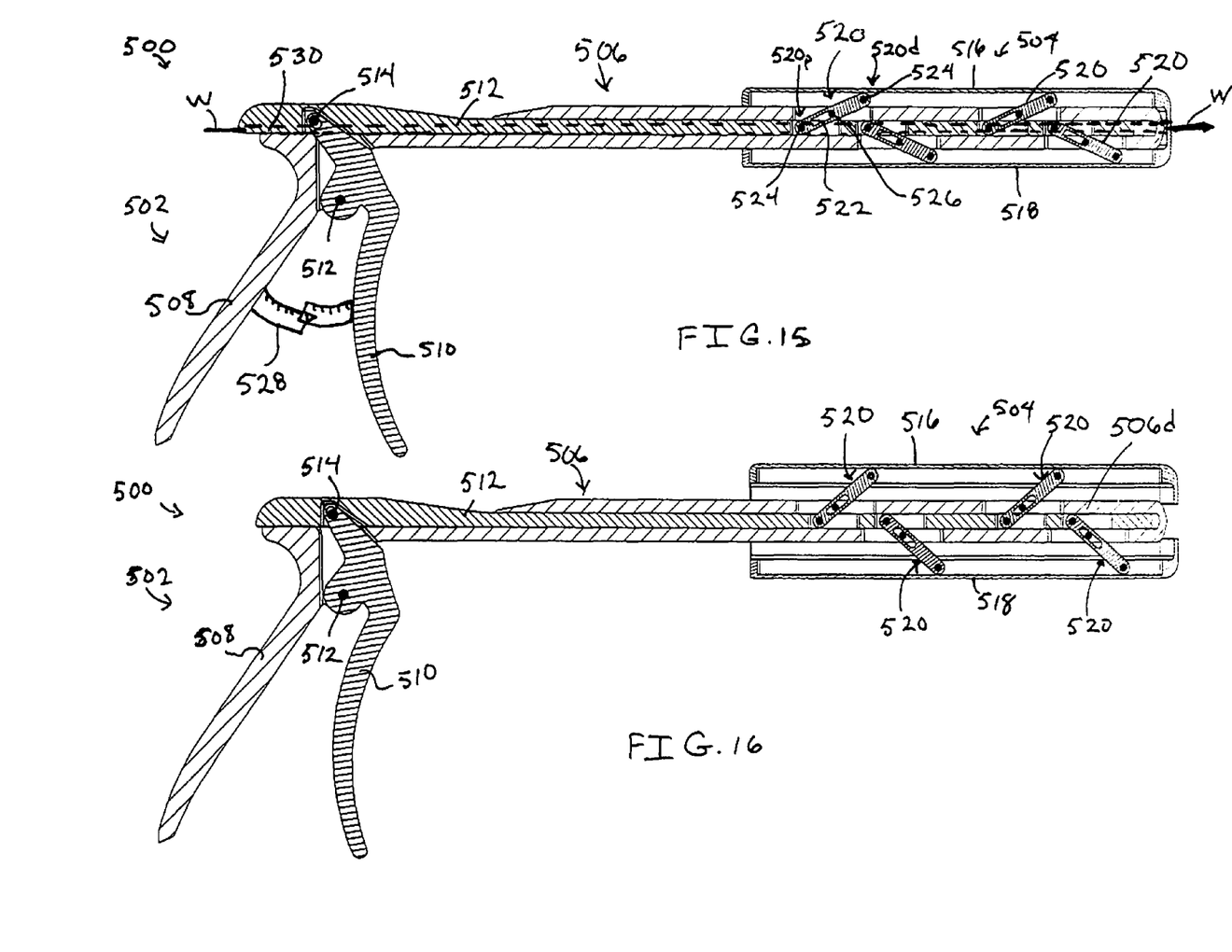
FIG. 15 is a side cross-sectional view of the sizing-distracting apparatus with the jaws in the approximated position.
FIG. 16 side cross-sectional view of the sizing-distracting apparatus with the jaws in the spaced apart position.

In operation, a user moves jaw members 516, 518 between approximated and spaced positions by actuating handle 502. To actuate handle 502, the user pivots movable handle member 510 toward stationary handle member 508. The pivotal movement of movable handle member 510 causes a distal translation of actuation shaft 512. In response to the distal translation of actuation shaft 512, the proximal ends 520p of each link 520 moves distally and the distal ends 520d of each link 250 moves away from actuation shaft 512. As distal and proximal ends 520d, 520p of each links 520 moves, the pins 526 slidably disposed in slots 522 guide the movement of links 520. In addition, when the distal ends 520d of links 520 move away from actuation shaft 512, they separate first and second jaw members 516, 518, thereby placing end effector 504 in the spaced apart position, as shown in FIGS. 14 and 16. The user may return the end effector to the approximated position (see FIGS. 13 and 15) by pivoting movable handle member 510 away from stationary handle member 508. The jaws 516, 518 move towards each other or away from each other while maintaining a substantially parallel arrangement between the jaws 516, 518.

As shown in FIG. 15, an embodiment of instrument 100 includes a gauge 528 for measuring a distance between first and second jaw members 516, 518. Further, instrument 100 may define a lumen 530 extending therethrough and adapted to receive a guidewire 'W'. During a surgical procedure, a surgeon employs instrument 100 to distract adjacent spinous processes 'P' and measure the space between adjacent spinous processes 'P', as described in regard to surgical instrument 200.

In an alternative embodiment, links 520 operatively connect distal region 506*d* of elongate portion 506 to only one of first and second jaw members 516, 518. In this embodiment, the actuation of handle 506 only moves one jaw member (516 or 518) relative to the other.

It will be understood that various modifications may be made to the embodiments of the presently disclosed percutaneous interspinous process devices. Therefore, the above description should not be construed as limiting, but merely as exemplifications of embodiments. Those skilled in the art will envision other modifications within the scope and spirit of the present disclosure.

What is claimed is:

1. A percutaneous interspinous process device for treating spinal conditions, comprising:
   a first section defining a first lateral surface, a first medial surface and a first lumen extending from the first lateral surface to the first medial surface;
   a second section defining a second lateral surface, a second medial surface and a second lumen extending from the second lateral surface; and
   a locking mechanism including an elongate member protruding from the first medial surface of the first section and a medial recess defined in the second medial surface of the second section, the elongate member including a barb at a medial end thereof and being positionable between expanded and compressed conditions, the elongate member defining at least one slit in a periphery of the elongate member whereby the at least one slit extends only partially through the elongate member, the at least one slit facilitating the movement of the elongate member between the expanded and compressed conditions and extending radially inward, the elongate member having a first diameter in the expanded condition and a second diameter in the compressed condition, the barb having a diameter smaller than at least one of the first and second diameters of the elongate member, the medial recess configured for securely receiving at least a portion of the elongate member, and the elongate member configured to maintain a predetermined distance between adjacent spinous processes.

2. The percutaneous interspinous process device of claim 1, wherein the barb includes a slit for facilitating compression thereof.

3. The percutaneous interspinous process device of claim 1, wherein the medial recess of the second section defines an abutting surface for supporting at least a portion of the barb.

4. The percutaneous interspinous process device of claim 1, wherein at least one of the first and second lateral surfaces has a convex shape.

5. The percutaneous interspinous process device of claim 1, wherein at least one of the first and second sections includes a wing extending from a central longitudinal axis of the percutaneous interspinous process device.

6. The percutaneous interspinous process device of claim 5, wherein the wing extends in at least one of caudad and cephalad directions.

7. The percutaneous interspinous process device of claim 1, wherein at least one of the first and second medial surfaces has a plurality of first teeth adapted for engaging tissue.

8. The percutaneous interspinous process device of claim 1, wherein the elongate member includes a quantity of resilient material disposed therein.

9. The percutaneous interspinous process device of claim 1, wherein at least one of the first and second lateral surfaces is flat.

10. The percutaneous interspinous process device for treating spinal conditions of claim 1, wherein the elongate member moves radially inward within a plane defined transverse to a longitudinal axis of the elongate member toward the compressed condition and moves radially outward within the plane defined transverse to the longitudinal axis of the elongate member toward the expanded condition.

11. The percutaneous interspinous process device for treating spinal conditions of claim 1, wherein each diameter is defined by the largest radial diameter of the respective elongate member and barb in each of the respective expanded and compressed conditions.

12. The percutaneous interspinous process device of claim 1, wherein a plurality of slits are disposed radially around the periphery of the elongate member.

13. The percutaneous interspinous process device of claim 12, wherein there are at least 3 slits disposed radially around the periphery of the elongate member.

14. The percutaneous interspinous process device of claim 1, wherein the elongate member is substantially hollow.

15. The percutaneous interspinous process device of claim 1, further comprising a compressible bladder positioned within the elongate member.

16. The percutaneous interspinous process device of claim 1, wherein the at least one slit facilitates the radial movement of the elongate member as the elongate member moves between radially expanded and radially compressed conditions, the elongate member maintaining a substantially uniform length as the elongate member moves between radially expanded and radially compressed conditions.

17. A surgical kit, comprising:
   a percutaneous interspinous process device for treating spinal conditions including a first section defining a first lateral surface, a first medial surface and a first lumen extending from the first lateral surface to the first medial surface; a second section defining a second lateral surface, a second medial surface, and a second lumen extending from the second lateral surface; and a locking mechanism including an elongate member protruding from the first medial surface of the first section and a medial recess defined in the second medial surface of the second section, the elongate member including a barb at a medial end thereof, at least one of the elongate member and the barb being positionable between expanded and compressed conditions in response to positioning within the medial recess, at least one of the elongate member and the barb defining at least one slit in a periphery of the at least one elongate member and barb whereby the at least one slit extends only partially through the at least one elongate member and barb, the at least one slit facilitating the movement of at least one of the barb and the elongate member between the expanded and compressed conditions, the at least one slit extending radially inward, wherein the medial recess is configured for securely receiving at least a portion of at least one of the barb and the elongate member such that the barb has a smaller diameter than the elongate member in at least one of the expanded and compressed conditions of at least one of the elongate member and the barb, wherein the elongate member is configured to define a space between adjacent spinous processes and maintain a predetermined distance between adjacent spinous processes; and a sizing instrument configured for determining the appropriate size of the percutaneous interspinous process device, wherein the sizing instrument is configured to measure a space between adjacent spinous processes.

18. The surgical kit of claim 17, wherein the sizing instrument includes an end effector having first and second jaws movable between a juxtaposed position and a spaced apart position.

19. The surgical kit of claim 18, wherein the sizing instrument includes a gauge operatively associated with the end effector, wherein the gauge is configured to measure a distance between the first and second jaws.

20. The surgical kit of claim 18, wherein the sizing instrument includes an actuation mechanism operatively connected to the end effector, wherein the actuation mechanism is adapted to move the first and second jaws between the juxtaposed position and the spaced apart position.

21. The surgical kit of claim 17, wherein the sizing instrument includes a bore extending therethrough, the bore being adapted to receive a guidewire.

22. The surgical kit of claim 17, wherein at least one of the elongate member and the barb moves radially inward within a plane defined transverse to a longitudinal axis of the elongate member toward the compressed condition and moves radially outward within the plane defined transverse to the longitudinal axis of the elongate member toward the expanded condition.

23. The surgical kit of claim 17, wherein each diameter is defined by the largest radial diameter of the respective elongate member and barb in each of the respective expanded and compressed conditions.

24. A percutaneous interspinous process device for treating spinal conditions, comprising:

a first section defining a first lateral surface, a first medial surface and a first lumen extending from the first lateral surface to the first medial surface;

a second section defining a second lateral surface, a second medial surface and a second lumen extending from the second lateral surface; and a locking mechanism including an elongate member protruding from the first medial surface of the first section and a medial recess defined in the second medial surface of the second section, the elongate member includes a barb at a medial end thereof, the barb being positionable between expanded and compressed conditions and having a first diameter in the expanded condition and a second diameter in the compressed condition, the barb defining at least one slit in a periphery of the barb whereby the at least one slit extends only partially through the barb, the at least one slit facilitating the movement of the elongate member between the expanded and compressed conditions and extending radially inward, the elongate member having a diameter larger than at least one of the first and second diameters of the barb, the medial recess configured for securely receiving at least a portion of the elongate member, and the elongate member configured to maintain a predetermined distance between adjacent spinous processes.

25. The percutaneous interspinous process device for treating spinal conditions of claim 24, wherein the barb moves radially inward within a plane defined transverse to a longitudinal axis of the elongate member toward the compressed condition and moves radially outward within the plane defined transverse to the longitudinal axis of the elongate member toward the expanded condition.

26. The percutaneous interspinous process device for treating spinal conditions of claim 24, wherein each diameter is defined by the largest radial diameter of the respective elongate member and barb in each of the respective expanded and compressed conditions.

* * * * *